United States Patent [19]

Mewshaw

[11] Patent Number: 5,756,521
[45] Date of Patent: May 26, 1998

[54] CHROMAN-2-YLMETHYLAMINO DERIVATIVES

[75] Inventor: Richard E. Mewshaw, South Brunswick, N.J.

[73] Assignee: American Home Products Corporation, Madison, N.J.

[21] Appl. No.: 816,585

[22] Filed: Mar. 13, 1997

Related U.S. Application Data

[60] Provisional application No. 60/014,778 Apr. 3, 1996.

[51] Int. Cl.⁶ .......... A61K 31/44; C07D 401/04; C07D 405/00
[52] U.S. Cl. .......... 514/337; 546/282.7; 546/283.1
[58] Field of Search .......... 514/337; 546/282.7, 546/283.1

[56] References Cited

PUBLICATIONS

Kerrigan et al, "Preparation of Aromatic Bicycle heterocyclic compounds as serotoninergic and dopaminergic receptor antogonists" CA123:340154 (1995).

Boettcher et al, "Preparation of arylaminesas central nervous system agents", CA125:58325, (1996).
Corsini et al., Adv. Biochem. Psychopharmacol, 16, 645–648, 1977.
Lahti et al., Mol. Pharm. 42, 432–438, 1993.
Tamminga et al., Science, 200, 567–568, 1978.
Tamminga et al., Psychiatry, 398–402, 1986.

Primary Examiner—Deborah C. Lambkin
Attorney, Agent, or Firm—Rebecca R. Barrett

[57] ABSTRACT

Compounds of the formula:

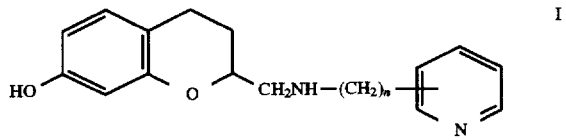

in which n is one of the integers 1, 2, 3 or 4, or a pharmaceutically acceptable salt thereof, are inhibitors of dopamine synthesis and release, useful in the treatment of schizophrenia, Parkinson's Disease, Tourette's Syndrome, alcohol addiction, cocaine addiction, and addiction to analogous drugs.

5 Claims, No Drawings

CHROMAN-2-YLMETHYLAMINO DERIVATIVES

BACKGROUND OF INVENTION

This application claims the benefit of U.S. Provisional Application No. 60/014.778, filed Apr. 3, 1996, now pending.

Efforts to induce antipsychotic activity with dopamine autoreceptor agonists have been successful (Corsini et al. Adv. Biochem. Psychopharmacol 16, 645–648, 1977; Tamminga et al. Science 200, 567–568, 1978; and Tamminga et al. Psychiatry 398–402, 1986). A method for determining intrinsic activity at the dopamine $D_2$ receptor was recently reported [Lahti et al., Mol. Pharm. 42, 432–438, (1993)]. Intrinsic activity is predicted using the ratio of the "low-affinity agonist" (LowAg) state of the receptor and the "high-affinity agonist" (HighAg) state of the receptor, i.e. LowAg/HighAg. These ratios correlate with the agonist, partial agonist, and antagonist activities of a given compound, which activities characterize a compounds ability to elicit an antipsychotic effect.

DESCRIPTION OF THE INVENTION

In accordance with this invention, there is provided a group of compounds which are useful antipsychotic agents. The compounds of this invention are essentially free from extrapyramidal side effects (EPS). The compounds of this invention are selective autoreceptor agonists, functioning primarily to activate only autoreceptors versus postsynaptic $D_2$ dopamine receptors). As such, they provide functional modulation of dopamine systems of the brain without the excessive blockade of the postsynaptic dopamine receptors, which have been observed to be responsible for the serious side effects frequently exhibited by agents found otherwise clinically effective for treatment of schizophrenia. Activation of the dopamine autoreceptors results in reduced neuronal firing a well as inhibition of dopamine synthesis and release and therefore provide a means of controlling hyperactivity of the dopaminergic systems.

More specifically, the compounds of this invention are depicted by the following Formula I:

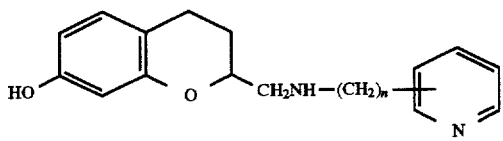

in which n is one of the integers 1, 2, 3 or 4 or a pharmaceutically acceptable salt thereof.

The pharmaceutically acceptable salts are those derived from such organic and inorganic acids as: acetic, lactic, citric, fumaric, tartaric, succinic, maleic, malonic, oxalic, hydrochloric, hydrobromic, phosphoric, nitric, sulfuric, methanesulfonic, methylbenzene sulfonic, and similarly known acceptable acids.

The compounds of Formula I are prepared by the overall sequence as follows:

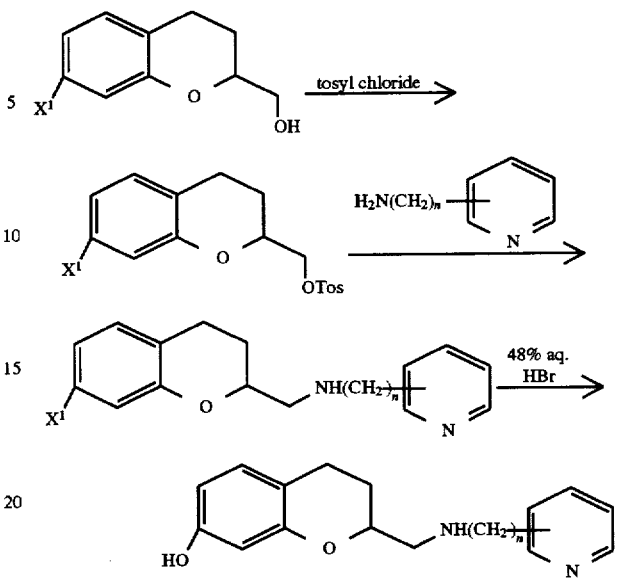

In this reaction sequence, $X^1$ is protected oxygen in which the protecting group is methyl, benzyl, and the like, known oxygen protecting groups. The final step of the reaction sequence involves deprotection of oxygen to provide the hydroxy group in 7-position of the benzopyran ring.

Specific exemplification of the production of a representative compound of this invention is given in the following procedure:

EXAMPLE 1

2-{[Pyridin-2-ylmethyl)-amino]-methyl}-chroman-7-ol

To a solution of 3,4-dihydro-7-methoxy-2H-1-benzopyran-2-methanol (23 g, 0.118 mol) in anhydrous pyridine (500 mL) was added p-toluenesulfonyl chloride (33.9 g, 0.78 mol). The reaction was allowed to stir for 2 days under nitrogen at room temperature then the solution was concentrated under vacuum. The crude product was diluted with $CH_2Cl_2$ (1 L) and washed with 1M $H_2SO_4$ (2×500 mL). The organic layer was washed with saturated aqueous sodium bicarbonate (1 L), brine (500 mL) and the organic layer dried and concentrated under vacuum to afford 34 g (92.2% yield) of (R,S)-3,4-dihydro-7-methoxy-2H-1-benzopyran-2-methyltosylate as a white solid: mp 67°–69° C.; MS (EI) m/z 348 (M+); $^1$H NMR (DMSO-$d_6$) d 1.51–1.65 (1H, m), 1.84–1.90 (1H, m), 2.41 (3H, s), 2.53–2.70 (2H, m), 3.66 (3H, s), 4.16 (1H, m), 4.26 (1H, m), 6.18 (1H, d, J=2.42 Hz), 6.38 (1H, dd, J=8.35, 2.64 Hz), 6.90 (1H, d, J=8.35), 7.48 (2H, d, J=8.57 Hz), 7.82 (2H, d, J=8.35).

A solution of 3,4-dihydro-7-methoxy-2H-1-benzopyran-2-methyltosylate (2.0 g, 6.4 mmol) and 4-aminomethyl pyridine (1.29 g, 11.9 mmol) in anhydrous DMSO (30 mL) was heated at 100° C. for 6 hours then poured into water (200 mL) and extracted with $CH_2Cl_2$ (2×150 mL). The combined organic layers were dried and the solvent removed under vacuum. Purification by flash chromatography (5% MeOH—$CH_2Cl_2$) afforded 1.2 g (68.9% yield) of 4-pyridinyl-(7-methoxy-chroman-2-ylmethyl)-amine as a thick oil: MS EI 284 (M+).

A solution of 4-pyridinyl-(7-methoxy-chroman-2-ylmethyl)-amine (1.2 g, 4.4 mmol) in 48% aqueous HBr (30 mL) was heated to reflux for 3 hours. The reaction mixture was then allowed to cool to room temperature and basified with 1N NaOH until pH 12. The basic reaction mixture was extracted with EtOAc (2×100 mL), dried and the solvent removed under vacuum. Chromatography (7% MeOH/$CH_2Cl_2$) afforded 540 mg of title compound (42.3% yield). The corresponding hydrogen oxalate salt was prepared in isopropanol, mp 210°–211° C.

Elemental analysis for $C_{16}H_{18}N_2O_2 \cdot (COOH)_2 \cdot 0.25\ H_2O$ Calc'd: C, 59.20; H, 5.66; N, 7.68 Found: C, 59.08; H, 5.51; N, 7.44.

The compounds of this invention are dopamine autoreceptor agonists, that is, they serve to modulate the synthesis and release of the neurotransmitter dopamine. They are thus useful for treatment of disorders of the dopaminergic system, such as schizophrenia, Parkinson's disease and Tourette's syndrome. Such agents are partial agonists at the postsynaptic dopamine $D_2$ receptor and are thereby useful in the treatment of alcohol and drug addiction.

Affinity for the dopamine autoreceptor was established by a modification of the standard experimental test procedure of Seemen and Schaus, European Journal of Pharmacology 203: 105–109, 1991, wherein homogenized rat striatal brain tissue is incubated with $^3$H-quinpirole (Quin.) and various concentrations of test compound, filtered and washed and counted in a Betaplate scintillation counter.

High affinity for the dopamine D-2 receptor was established by the standard experimental test procedure of Fields, et al., Brain Res., 136, 578 (1977) and Yamamura et al., eds., Neurotransmitter Receptor Binding, Raven Press, N.Y. (1978) wherein homogenized limbic brain tissue is incubated with $^3$H-spiroperidol (Spiper.) and various concentrations of test compound, filtered and washed and shaken with Hydrofluor scintillation cocktail (National Diagnostics) and counted in a Packard 460 CD scintillation counter.

The results of these tests with the representative compound of this invention prepared in Example 1 were $IC_{50}$ (nM), $D_2$, (Quin.)=2.21; $IC_{50}$ (nM), (Spiper.)=1231; ratio= 557

Hence, the compounds of this invention effect the synthesis of the neurotransmitter dopamine and thus are useful in the treatment of dopaminergic disorders such as schizophrenia, Parkinson's Disease, Tourette's Syndrome, alcohol addiction, cocaine addiction, and addiction to analagous drugs.

Applicable solid carriers for pharmaceutical compositions containing the compounds of this invention can include one or more substances which may also act as flavoring agents, lubricants, solubilizers, suspending agents, fillers, glidants, compression aids, binders or tablet-disintergrating agents or an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. Oral administration may be either liquid or solid composition form.

Preferably the pharmaceutical composition is in unit dosage form, e.g. as tablets or capsules. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

The dosage to be used in the treatment of a specific psychosis must be subjectively determined by the attending physician. The variables involved include the specific psychosis and the size, age and response pattern of the patient.

What is claimed is:

1. A compound of the formula:

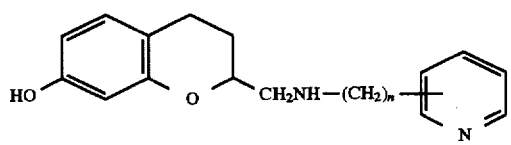

in which n is one of the integers 1, 2, 3 or 4 or a pharmaceutically acceptable salt thereof.

2. The compound of claim 1 which is 2-{[pyridin-4-yl-methylamino]-methyl}-chroman-7-ol or a pharmaceutically acceptable salt thereof.

3. A pharmaceutical composition of matter comprising a compound of the formula:

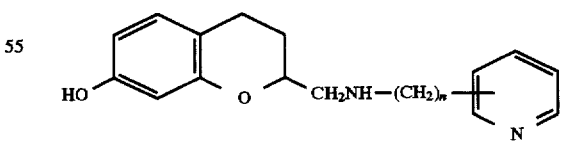

in which n is one of the integers 1, 2, 3 or 4 or a pharmaceutically acceptable salt thereof and a pharmaceutically acceptable carrier therefor.

4. A method for reducing dopamine synthesis and release in a patient suffering from hyperactivity of the dopaminergic systems, which comprises administering to said patient a compound of the formula:

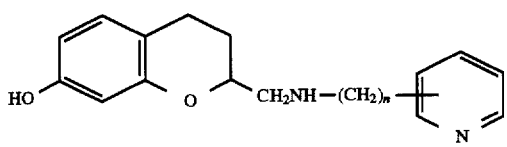

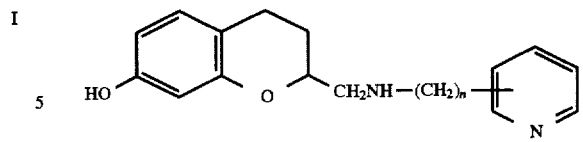

in which n is one of the integers 1, 2, 3 or 4 or a pharmaceutically acceptable salt thereof, in an amount sufficient to modulate the dopamine systems of the brain.

5. A method for treating schizophrenia which comprises administering to a patient suffering from schizophrenia, orally or parenterally, a compound of the formula:

in which n is one of the integers 1, 2, 3 or 4 or a pharmaceutically acceptable salt thereof, in an amount sufficient to alleviate the symptoms of schizophrenia.

* * * * *